(12) United States Patent
Gil

(10) Patent No.: US 10,695,452 B2
(45) Date of Patent: Jun. 30, 2020

(54) DEVICE FOR CLEANING A HEARING AID

(71) Applicant: MG DEVELOPPEMENT, Perols (FR)

(72) Inventor: Jose Gil, Saint Bauzille de Montmel (FR)

(73) Assignee: MG DEVELOPMENT, Perols (FR)

( * ) Notice: Subject to any disclaimer, the term of this patent is extended or adjusted under 35 U.S.C. 154(b) by 214 days.

(21) Appl. No.: 15/565,395

(22) PCT Filed: Feb. 8, 2017

(86) PCT No.: PCT/FR2017/050280
§ 371 (c)(1),
(2) Date: Oct. 9, 2017

(87) PCT Pub. No.: WO2017/137695
PCT Pub. Date: Aug. 17, 2017

(65) Prior Publication Data
US 2018/0126020 A1    May 10, 2018

(30) Foreign Application Priority Data

Feb. 8, 2016 (FR) ...................................... 16 50974
Feb. 8, 2016 (FR) ...................................... 16 50977

(51) Int. Cl.
| A61L 2/00 | (2006.01) |
| B08B 9/00 | (2006.01) |
| B08B 3/04 | (2006.01) |
| B08B 3/00 | (2006.01) |
| A61L 2/18 | (2006.01) |
| B08B 3/10 | (2006.01) |

(52) U.S. Cl.
CPC ................ *A61L 2/18* (2013.01); *B08B 3/102* (2013.01); *A61L 2202/24* (2013.01); *H04R 2460/17* (2013.01)

(58) Field of Classification Search
CPC ..... A61L 2/00; A61L 2/04; A61L 2/18; A61L 2202/00; B08B 3/04
USPC ...... 422/28, 292, 301, 307; 134/22.1, 104.2, 134/105, 166 R, 198, 110; 381/60
See application file for complete search history.

(56) References Cited

U.S. PATENT DOCUMENTS

2008/0253579 A1* 10/2008 Cronin ................... H04R 25/30
                                                                381/60
2010/0189598 A1    7/2010  Fraundorfer
2013/0220385 A1    8/2013  Gil

* cited by examiner

*Primary Examiner* — Monzer R Chorbaji
(74) *Attorney, Agent, or Firm* — Craft Chu PLLC; Andrew W. Chu

(57) ABSTRACT

The device for cleaning a hearing aid by contact with a liquid includes a cleaning cavity suitable for receiving the end piece of the hearing aid and that is provided, at the bottom of same, with an opening for discharging the liquid. The cleaning cavity is defined laterally by an inner skin surrounded by an outer skin, the outer skin including an injector for the liquid while the inner skin defines, at the base of same, an opening overhanging the bottom and allowing the liquid to pass into the cleaning cavity. The invention also concerns an assembly includes the cleaning device and a reloading unit, the reloading unit being suitable for filling a tank of the cleaning device.

17 Claims, 7 Drawing Sheets

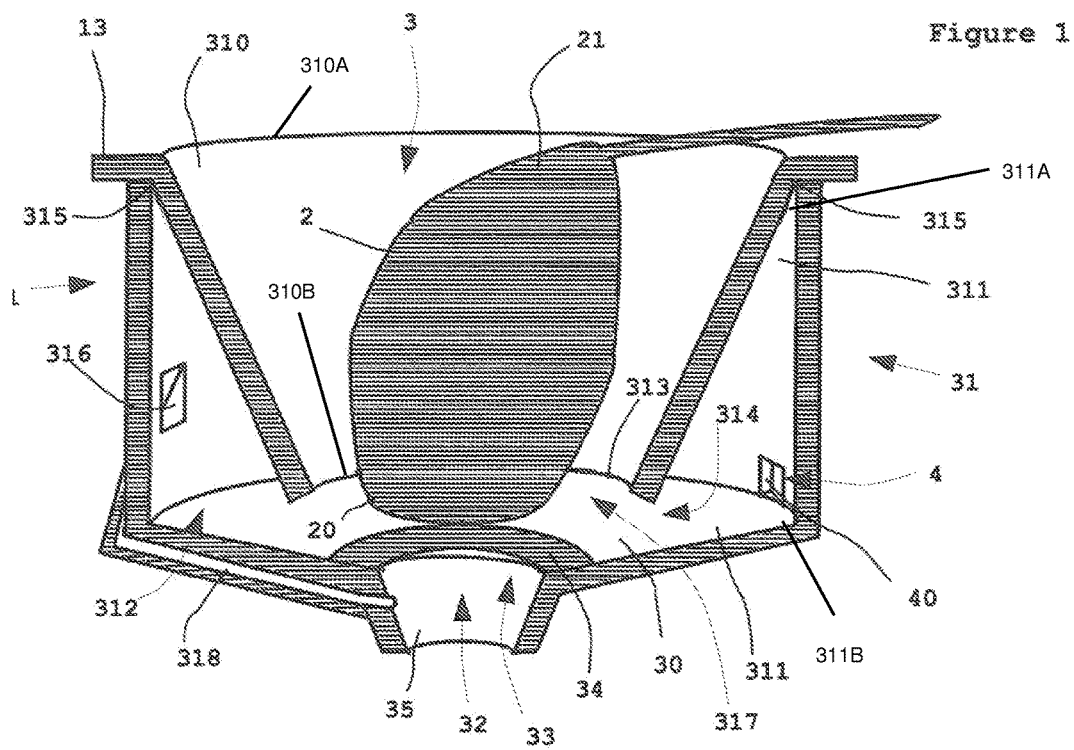
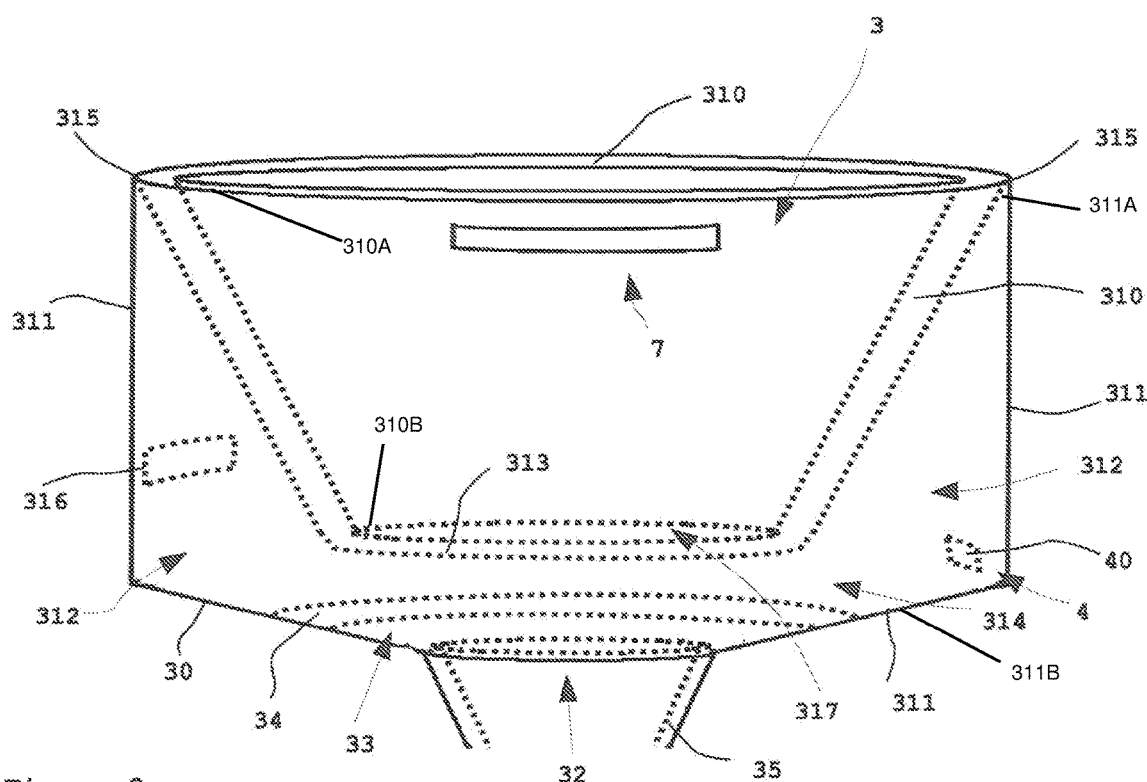

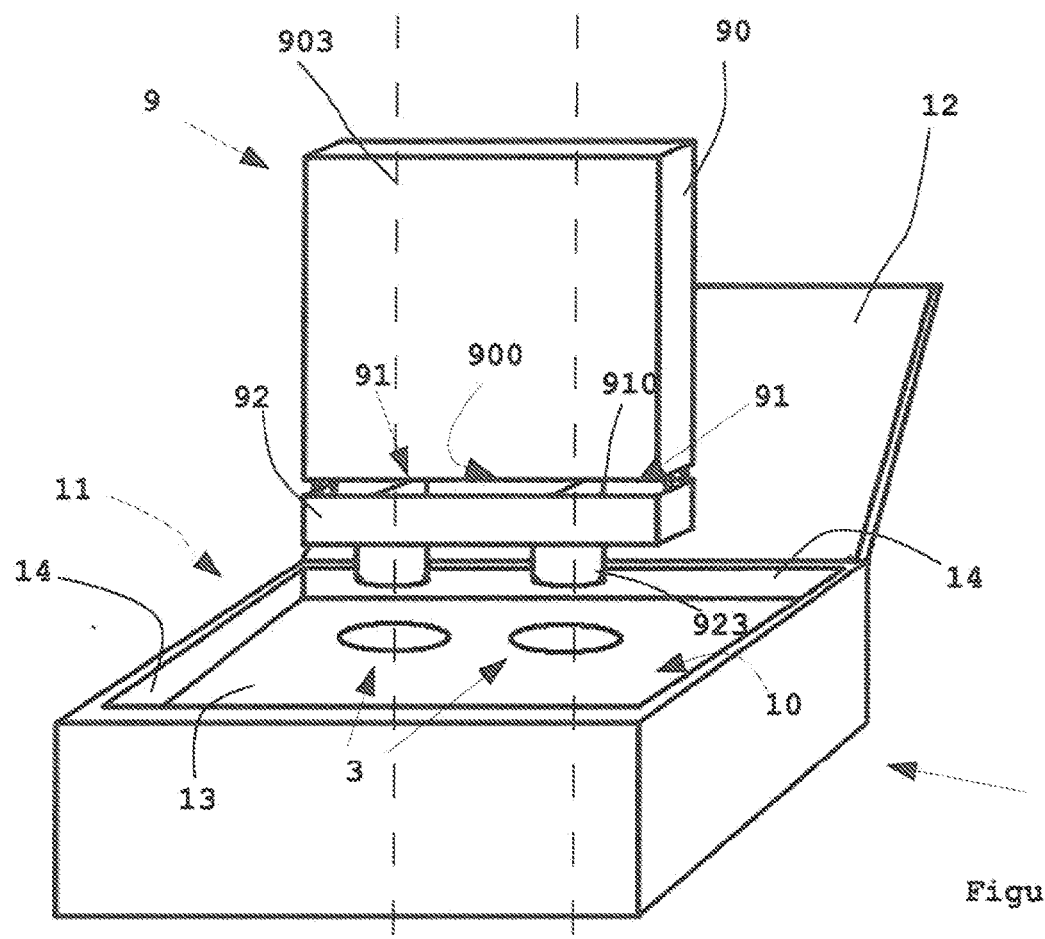
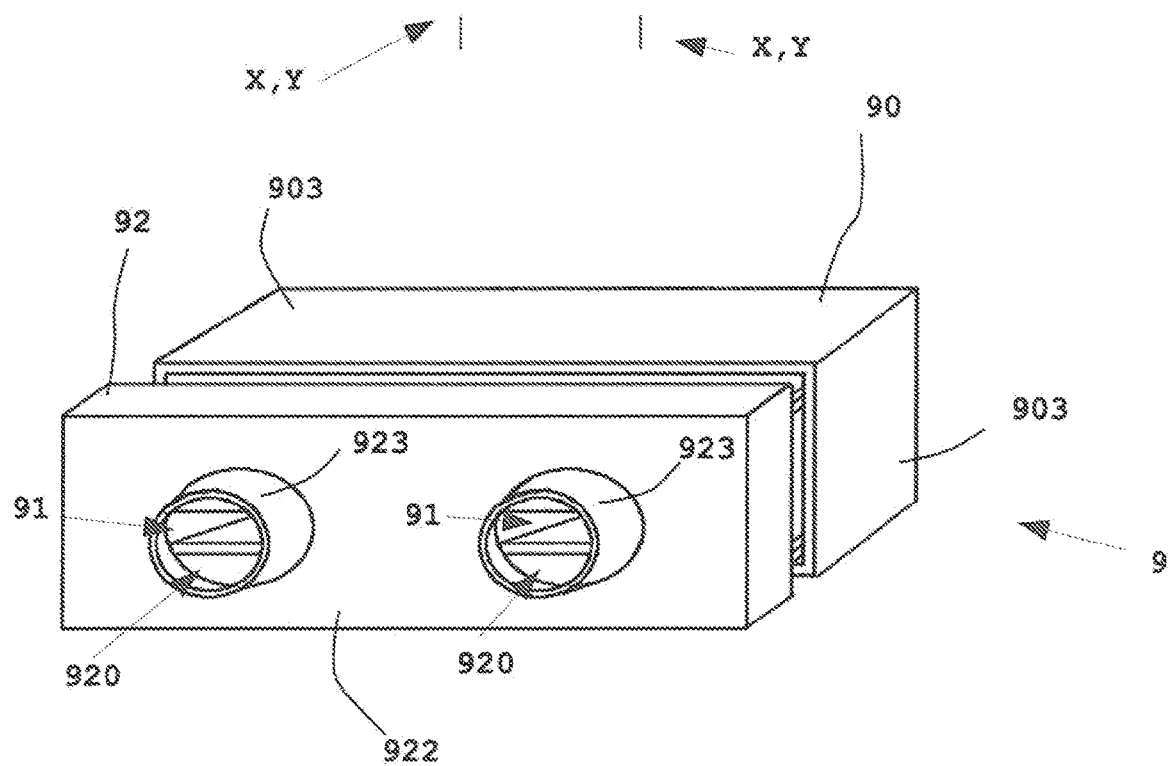

DEVICE FOR CLEANING A HEARING AID

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention is related to the field of the cleaning of a hearing aid.

2. Description of Related Art Including Information Disclosed Under 37 CFR 1.97 and 37 CFR 1.98

Being worn on a daily basis, an earmold of a hearing aid is regularly contaminated with earwax and/or impurities. Now, an earmold of a dirty hearing aid has a loss of efficiency and is likely to cause irritation in the auditory canal. In order to guarantee the proper operation of the hearing aid and the comfort of the person wearing it, it is necessary to proceed to a regular cleaning of this earmold.

At least two types of hearing aid earmold are known, a first type of earmold comprises electronic elements permitting to perform the transmission or amplification of the sounds perceived by the prosthesis. To this end, the earmold comprises a distal portion intended to be into contact with the auditory canal and a proximal portion connecting the earmold to an ear contour. The ear contour, intended to be placed behind the ear of a user, includes electrical power supply means, a switch, etc.

A second type of earmold includes all the technical and electronic components of a hearing aid, thus, the earmold alone constitutes the hearing aid and does not need to be connected to an ear contour.

In general, since electronic elements are likely to be damaged during a prolonged exposure to a cleaning liquid (for example water, a cerumenolytic solution including disinfecting properties, etc.), it is preferable to avoid performing the cleaning of the earmold by complete immersion in a cleaning liquid. This is particularly the case for the second type of earmold, which includes a larger number of electronic elements than the first one.

To this end, a cleaning device exists, which is described in FR 2 966 046 and implements a method for cleaning by touching the earmold by generating a vortex of liquid around the earmold. To this end, the cleaning device comprises an accommodation recess adapted to hold the earmold in a cleaning cavity. The cleaning cavity is designed so as to generate a vortex of liquid around the earmold when it is in its accommodation recess. To this end, the cleaning cavity comprises a liquid-injecting nozzle adapted to inject liquid into the cleaning cavity, liquid-directing means (e.g. grooves or fins) permitting to direct the flow of liquid, and a hole for discharging the liquid located in front of the accommodation recess and having the effect of centering the eye of the vortex under the earmold of the prosthesis.

However, such a cleaning device has the drawback of having a complex structure, making its industrialization difficult.

In addition, the recess accommodating the earmold must be perfectly fitted for such an earmold so that only the distal portion to be cleaned emerges through the opening under the accommodation recess and so as to prevent any rise of cleaning fluid through this opening at the level of the proximal portion.

Now, it should be reminded that a wide variety of earmolds are available on the market, which earmolds are distinguished by their diversity in shape determined by that of the user's auditory canal, in order to guarantee as well as possible his comfort when wearing the hearing aid. It is therefore necessary for the manufacturer of such cleaning devices to provide, for his devices, a multiplicity of different accommodation recesses with a shape strictly adapted to this diversity of earmold shapes. This inevitably generates additional manufacturing costs that have a repercussion on the final cost of the cleaning device. Moreover, in some extreme cases, it may be found that none of the different accommodation recesses provided by the manufacturer of the cleaning device is suitable. It may also happen that the user replaces an earmold with another earmold with a different shape, in which case the shape of the accommodation recess originally provided no longer matches. The user may thus sometimes be obliged to have a tailor-made accommodation recess molded to the precise shape of the earmold by his own means, and to support all the costs related to such an embodiment. This is not only constraining, but also particularly expensive.

BRIEF SUMMARY OF THE INVENTION

The present invention pretends to cope with these drawbacks through a simple technical solution, with a reduced manufacturing cost and, in addition, avoiding the need for a strict adjustment of the recess accommodating the earmold to the specific shape of the latter.

To this end, the present invention includes a universal cleaning cavity, in which all types of earmolds can be inserted. However, cleaning an earmold with a specific shape in a universal cleaning cavity by touching with a vortex of liquid raises a new technical problem: how to create a vortex of liquid within a universal cleaning cavity permitting to carry out a cleaning by touching earmolds of all shapes while effectively protecting each type of earmold and namely their proximal portion from the projections of liquid inherent in the formation of a vortex of liquid and in the instability of a vortex of liquid.

To this end, the present invention pretends to provide a solution permitting to manage the flow of cleaning liquid that is injected into the cleaning cavity, in order to ensure the cleaning of the distal portion of the earmold by touching with a vortex of liquid, without any risk of substantial splashing onto the proximal portion of the earmold and of submersion of the earmold.

Thus, through an inventive step it has in particular been conceived that the injection of cleaning liquid occurs at the level of an outer skin surrounding an inner skin, which delimits the cleaning cavity and perfectly protects the earmold against all projections of liquid, the inner skin delimiting at its base an opening permitting the passing through of the liquid from the outer skin to the cleaning cavity. Thus, a displacement of liquid is generated within the cleaning cavity and permits to clean the earmold by touching with cleaning liquid. Preferably, the displacement of cleaning liquid is circular and forms a vortex around the distal end of the earmold.

In this respect, a first aspect of the invention relates to a device for cleaning a hearing aid by touching with a liquid, the cleaning device comprising a cleaning cavity adapted to accommodate the earmold and which is provided at its bottom with a hole for discharging the liquid, wherein the cleaning cavity is laterally delimited by an inner skin surrounded by an outer skin, the outer skin including means for injecting the liquid, while the inner skin delimits, at its base, an opening overhanging the bottom and permitting the liquid to pass into the interior of the cleaning cavity.

Advantageously, the injection of cleaning liquid occurs at the level of the outer skin, while the inner skin perfectly protects the earmold from any projections of cleaning liquid and permits to generate a flow of liquid moving towards the earmold, which promotes a cleaning of the earmold by touching and facilitates the dissolution of earwax present on the surface of the earmold.

According to a first feature of the first aspect of the invention, the outer skin includes, at a level higher than the injection means, a lateral discharge hole permitting to discharge an excess of liquid circulating between the inner and outer skins. This lateral hole acts as an overflow and permits to control the maximum height of cleaning liquid between the inner and outer skins and, accordingly, in the cleaning cavity. Advantageously, the lateral hole controls the height of the flow of liquid, which permits to avoid any risk of submersion of the earmold.

According to a second feature of the first aspect of the invention, the liquid-injection means are tangent to the outer skin so as to project the liquid tangentially along the outer skin. This feature contributes to the creation of the liquid flow between the inner and outer skins, thus protecting the earmold from any projections of liquid.

According to a third feature of the first aspect of the invention, the cleaning device comprises a reservoir provided with a plug movable between a closed position, in which the liquid is confined in the reservoir, an open position, in which the liquid circulates between the cavity and the reservoir, and an emptying position, in which the liquid is drained from the reservoir out of the cleaning device. This feature permits the user of the cleaning device to transport the full container when the plug is in the closed position.

According to a fourth feature of the first aspect of the invention, the bottom comprises means for receiving the protruding earmold and adapted to receive the earmold in a raised way with respect to the bottom. This feature has the effect of raising the earmold with respect to the bottom of the cleaning cavity and thus contributes, on the one hand, to correctly positioning the earmold within the cavity and, on the other hand, to prevent the flow of liquid from submerging the earmold.

According to a peculiarity of the fourth feature of the first aspect of the invention, the receiving means are formed by a radial bar.

According to a fifth feature of the first aspect of the invention, the inner and outer skins form between them an annular space, which is closed at the top.

According to a sixth feature of the first aspect of the invention, the outer skin comprises means for projecting air into the annular space. This feature permits to quickly dry the earmold after a cleaning cycle. Moreover, the fact that the air-projecting means are located between the outer skin and the inner skin permits to put the air into whirling circulation and to thus optimize the drying of the earmold after a cleaning cycle.

According to a peculiarity of the sixth feature of the first aspect of the invention, the cleaning device comprises heating means heating the flow of the projected air.

According to a seventh feature of the first aspect of the invention, the cleaning device comprises a UVC lamp adapted to diffuse UVC waves towards the hearing aid so as to carry out a disinfection by UVC irradiation.

According to an eighth feature of the first aspect of the invention, the reservoir includes means for detecting the level of the liquid, these detecting means being adapted to trigger the emission of a warning signal when the liquid level present inside the reservoir reaches a predefined threshold level.

A second aspect of the invention relates to an assembly comprising a cleaning device according to the first aspect of the invention and a cleaning liquid refilling unit adapted to fill a reservoir of the cleaning device.

Advantageously, the refilling unit includes a sleeve adapted to cooperate with at least one cleaning cavity of the cleaning device so as to transfer the cleaning liquid from the refilling unit to the reservoir of the cleaning device.

The cooperation between a sleeve of the refilling unit and the cleaning cavity of the cleaning device promotes a transfer of the cleaning liquid under gravitation from the refilling unit to the reservoir of the cleaning device under gravitation. In addition, this cooperation permits a filling of the tank without splashes, particularly suitable for people with reduced dexterity such as elderly or handicapped persons.

According to a first embodiment of the second aspect of the invention, the refilling unit includes, on the one hand, a tank provided with an opening closed by a lid and, on the other hand, connecting means, which are adapted to perforate the lid when they are brought into connection with a cleaning cavity of the cleaning device.

According to a second embodiment of the second aspect of the invention, the refilling unit includes a cap, which comprises a channel, a perforator adapted to perforate the lid and means for connecting with the cleaning cavity, the cap being movable with respect to the tank between a preliminary position, in which the perforator is moved away from the opening and a percussion position, in which the perforator pierces the lid and releases the liquid through the channel.

Advantageously, this refilling unit permits, when the cap is maintained in the preliminary position, to tightly keep the liquid inside the tank and to control both the perforation of the cap and the flow of the liquid which results therefrom. In addition, its use permits to limit the volume of the cleaning device and therefore the size of the latter since it is no longer necessary to provide inside the latter for a space large enough to accommodate the refilling unit.

According to a third embodiment of the second aspect of the invention, the perforator defines a cannula for causing the cleaning liquid contained in the tank to flow through the channel of the cap to the cleaning cavity. This feature permits to limit the flow of liquid when it flows out of the refilling unit, thus avoiding any unintentional splashing.

According to a fourth embodiment of the second aspect of the invention, the perforator extends in the direction of displacement of the cap and has two lateral faces connected to each other by a base including a perforating tip capable of perforating the lid.

According to a fifth embodiment of the second aspect of the invention, the perforator compartmentalizes the channel of the cap into a central zone located between two lateral faces of the perforator and two lateral zones each located between a lateral face and an edge of the channel. This feature promotes a clean filling of the reservoir of the cleaning device, the lateral zones creating an air intake, which permits the liquid to flow by gravity through the central zone corresponding to the flow cannula defined by the perforator.

BRIEF DESCRIPTION OF THE SEVERAL VIEWS OF THE DRAWINGS

Other features and advantages of the present invention will become clear from the following detailed description of an exemplary embodiment given as an indication and non-restrictive.

The understanding of this description will be facilitated when referring to the seven attached drawings.

FIG. 1 is a schematic cross-sectional view of a representation of a cleaning cavity of the cleaning device according to the invention, the cleaning cavity containing an earmold.

FIG. 2 is a three-dimensional schematic view of a representation of the cleaning cavity of FIG. 1.

FIG. 8 is a perspective view, before the filling, of a cleaning device shown in FIGS. 4 to 7 and of a refilling unit according to the invention, in which the cap is placed in the preliminary position.

FIG. 9 is a bottom plan view of the refilling unit of FIG. 8.

DETAILED DESCRIPTION OF THE INVENTION

Figure 3:
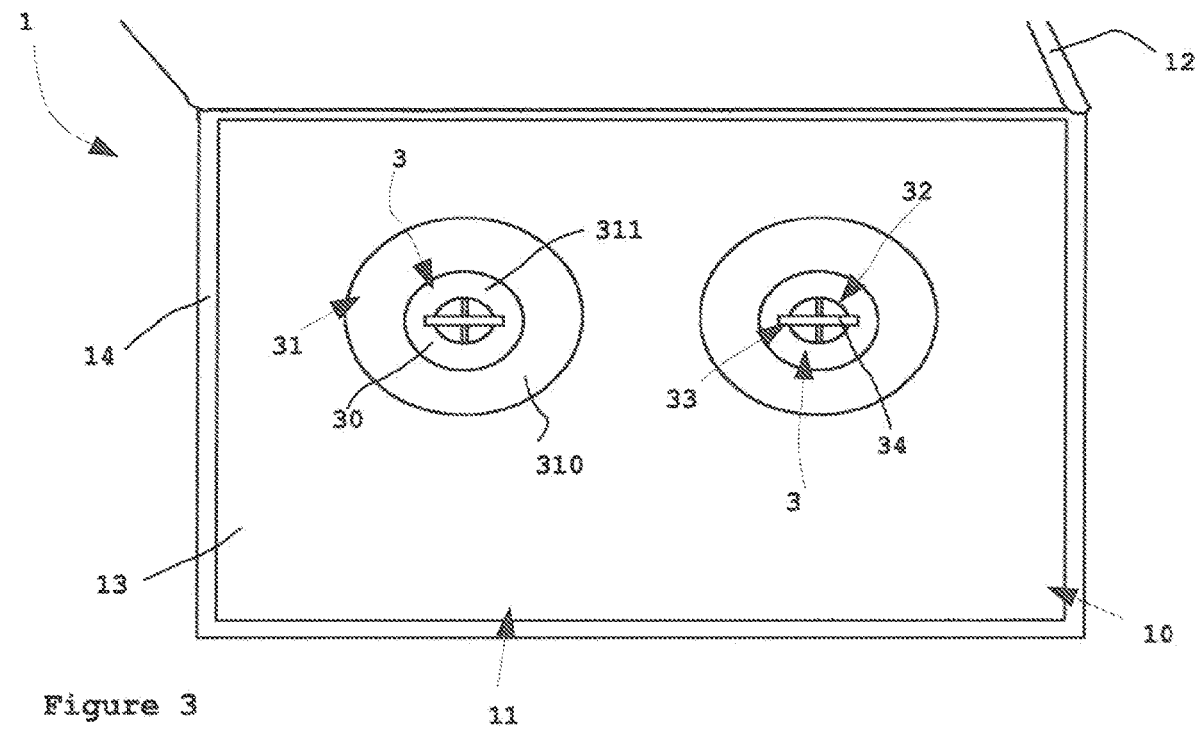
FIG. 3 is a top plan view of a cleaning space of a cleaning device according to the invention.

The invention relates to a cleaning device 1 for cleaning at least one hearing aid 20 and namely its earmold 2 (shown in FIG. 1).

The hearing aid 20 and more particularly the earmold 2 includes a number of electronic amplifying and/or transmitting components. The earmold 2 has a distal portion 21 designed to insert into the auditory canal of a user and a proximal portion 22 that is generally positioned at the front of the auditory canal. In the present example, the proximal portion 22 connects the earmold 2 to an ear contour 23 carried by the contour of a user's ear. However, the device according to the invention is also designed for cleaning an earmold of the second type (without an ear contour).

The cleaning device 1 is adapted to perform a cleaning of the hearing aid 20, and more particularly of the earmold 2, and yet more particularly of the distal portion 21 by touching with a vortex of liquid. The liquid touching the distal portion 21 releases the earwax and other impurities from the earmold 2 by dissolution. It should be noted that some (cerumenolytic) cleaning liquids also have disinfecting properties in order to eliminate irritant or allergenic substances present on the surface of the earmold 2.

To this end, the cleaning device 1 includes a cleaning space 10 located on the upper face 11 of the cleaning device 1. The latter is provided with a cover 12 movable between two positions, an open position, in which the cleaning space 10 is accessible for a user, and a closed position, in which the cover 12 delimits the cleaning space 10 at the top. The cleaning space 10 is also delimited at the bottom by a plate 13 and laterally by edges 14.

Advantageously, the cleaning space 10 is provided with at least one cleaning cavity 3 with a cylindrical or conical shape. Advantageously, the shape and the dimensions of the cleaning cavity 3 are adapted to accommodate all shapes of earmolds 2. In the variant embodiment shown, in order to simultaneously clean two earmolds 2, the cleaning device 1 includes two cleaning cavities 3. Each cleaning cavity 3 is formed in the plate 13 of the cleaning space 10.

In the example shown in FIGS. 1 and 2, the cleaning cavity 3 is shaped so as to receive in the center of its bottom 30 the distal portion 21 of the earmold 2. Thus, the user inserts each earmold 2 into a cleaning cavity 3 and deposits the ear contour 23, when the prosthesis includes one, on the plate 14 of the cleaning space 10. Once each hearing aid 20 is correctly positioned, the user closes the lid 12 of the cleaning space 10 and starts the cleaning cycle by pressing a button for activating the cleaning cycle.

Advantageously, the cleaning device 1 is adapted to perform a cleaning of the earmold 2 by touching with a vortex of liquid.

According to the invention, the cleaning device 1 includes a double-skin wall 31 having an inner skin wall or inner skin 310, for example with a V-shaped cross-section, which delimits the cleaning cavity 3 laterally and the upper end of which is connected to the upper end of an outer skin wall or outer skin 311, for example with a U-shaped cross-section. In fact, as shown in FIG. 1, the inner skin wall or inner skin 310 having an inner skin upper end 310A and an inner skin lower end 310B, delimits at its base 313 an opening 317 located over, on the one hand, the bottom 30 of the cavity 3, which is formed by a portion of the outer skin 311, having an outer skin upper end 311A and an outer skin bottom 30 with an outer skin bottom opening 32, the outer skin bottom being opposite said outer skin upper end so as to form a bottom of said cleaning cavity, and, on the other hand, a hole for discharging 32 cleaning liquid, which the bottom 30 includes.

The expression "the opening 317 located over the outer skin bottom 30" means that the opening 317 extends in a plane positioned directly above the outer skin bottom 30 or bottom of the cleaning cavity 3.

The cavity 3 is shaped so as to be able to accommodate any earmold 2 of any shape in such a way that its distal end 21 emerges through the opening 317 delimited by the inner skin wall or inner skin 310 located at a determined distance from the bottom 30 of the cavity 3.

Furthermore, such a structure of the double-skin wall 31 has the effect of providing between the inner skin wall or inner skin 310 and the outer skin wall or outer skin 311 an annular space 312, which circles the cleaning cavity 3 and which communicates with the latter at a level of a transit space 314 extending between the opening 317 delimited by the base 313 of the inner skin 310 and the bottom 30 of the cavity 3.

The annular space 312 is closed at the top by a junction 315 extending between the respective upper ends (inner skin upper end 310A and said outer skin upper end of the inner 310 and outer 311 skins.

Advantageously, the hole for discharging 32 cleaning liquid plays two roles, its first role consisting in discharging the cleaning liquid present in the cleaning cavity 3, and its second role consists, due to its centered position in the bottom 30 of the cleaning cavity 3, in centering the vortex of liquid in the center of the cleaning cavity 3.

According to the invention, this cleaning device 1 also includes means 4 for injecting liquid arranged in the annular space 312 between the two skins 310, 311 of the double-skin wall 31. The injection of the cleaning liquid at the level of the annular space 312 avoids any projections of liquid onto the proximal portion 22 of the earmold 2, this proximal portion 22 being protected by the inner skin 310 of the double wall 31.

In the example shown in FIGS. 1 and 2, the injection means 4 are formed by an injection nozzle 40, however, the injection means 4 can be formed by any means permitting to project liquid under pressure.

In the example shown in FIGS. 1 to 7, the injection means 4 are adapted to generate a vortex of liquid inside the cleaning cavity 3. To this end, the injection means 4 are arranged tangentially to the outer skin 311 thus projecting the liquid tangentially along the latter.

Consequently, once projected along the outer skin 311, due to the presence of the annular space 312, the liquid flow is forced to start rotating. In addition, the bottom 30 has a slope up to the discharge hole 32. This slope of the bottom 30 directs the rotating flow of liquid towards the discharge hole 32, the flow of liquid then circulating from the annular space 312 towards the bottom 30 of the cleaning cavity 3 while passing through the transit space 314.

Advantageously, the kinetics of the rotating flow of liquid permits to delay the discharge of the liquid through the discharge hole 32. Moreover, the supply of liquid is continuous during a cleaning cycle, the volume of rotating liquid increases and feeds the vortex the level of which rises both in the cleaning cavity 3 and in the annular space 312. In this way, the vortex of liquid, the eye of which is centered on the discharge hole 32, touches the earmold 2 and dissolves the earwax, which is present on its surface. In order to stabilize and maintain the liquid vortex, the flow of liquid injected into each cleaning cavity 3 is continuous and injected under constant pressure throughout the cleaning cycle.

Advantageously, and as shown in FIGS. 1 and 2, the cleaning device 1 comprises a lateral discharge hole 316 arranged in the annular space 312. Preferably, the lateral discharge hole 316 is arranged in the outer skin 311 at a threshold height defined so as to discharge a too large flow of liquid circulating in the annular space 312. The lateral discharge hole 316 is arranged at a height higher than that of the injection means 4. This results into this lateral discharge hole 316 acting as an overflow, permitting to control the flow of liquid circulating in the annular space 312 and, hence, to control the height of the vortex of liquid in the cleaning cavity 3. This feature permits to prevent the earmold 2 from being submerged by the vortex of liquid.

In the example shown in FIGS. 1 to 3, the cleaning device 1 includes means 33 for receiving the distal portion 21 of the earmold 2. These receiving means 33 extend protruding above of the discharge hole 32 and permits to raise the earmold 2 so that it does not enter into contact with the bottom 30 of the cleaning cavity 3. Thus, the earmold 2 does not contravene the circulation of the flow of liquid and permits the formation of the vortex of liquid. Preferably, the receiving means 33 are formed by at least one radial bar 34. However, the receiving means 33 can be formed by any mechanical means permitting to raise the earmold 2 so that it is not into contact with the discharge hole 32. Thus, irrespective of the shape of the earmold 2, its distal portion 21 will be positioned and held in the center of the cleaning cavity 3 in the same way.

Figure 4:
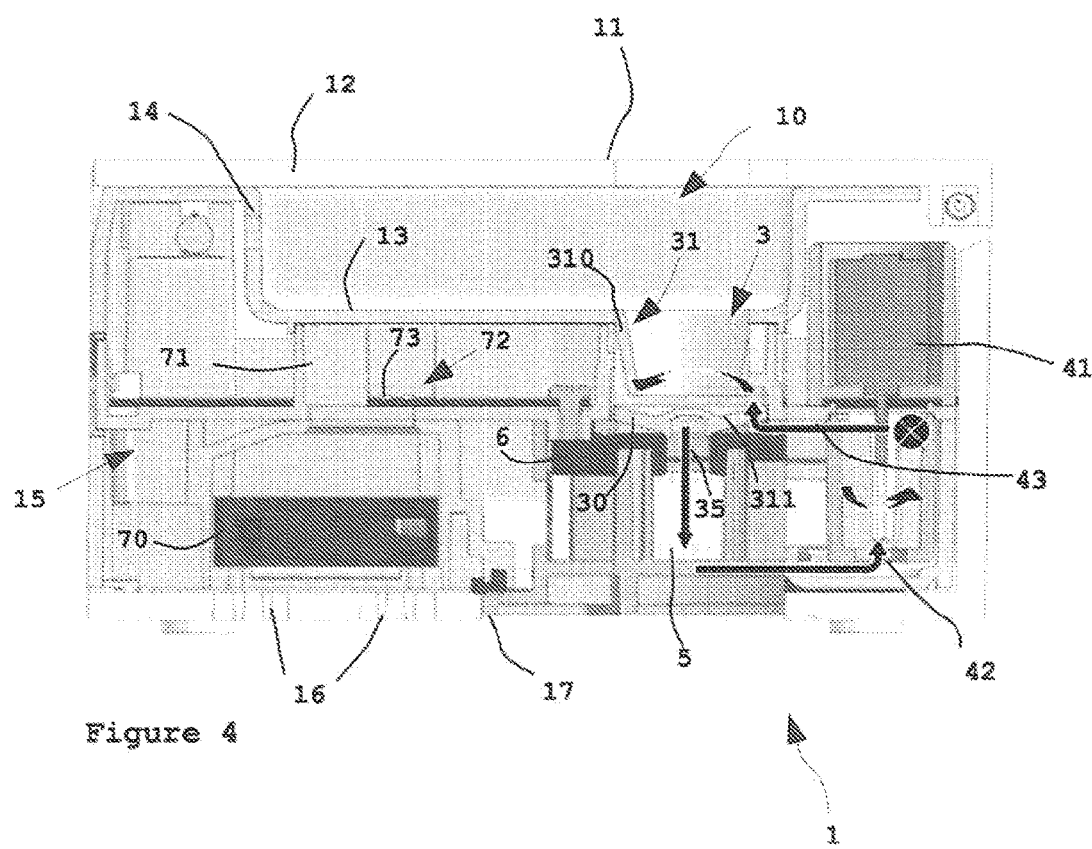
FIG. 4 is a cross-sectional view of the cleaning device according to the invention, in which the arrows show the circulation of the liquid flow during the cleaning of the earmold.
Figure 6:
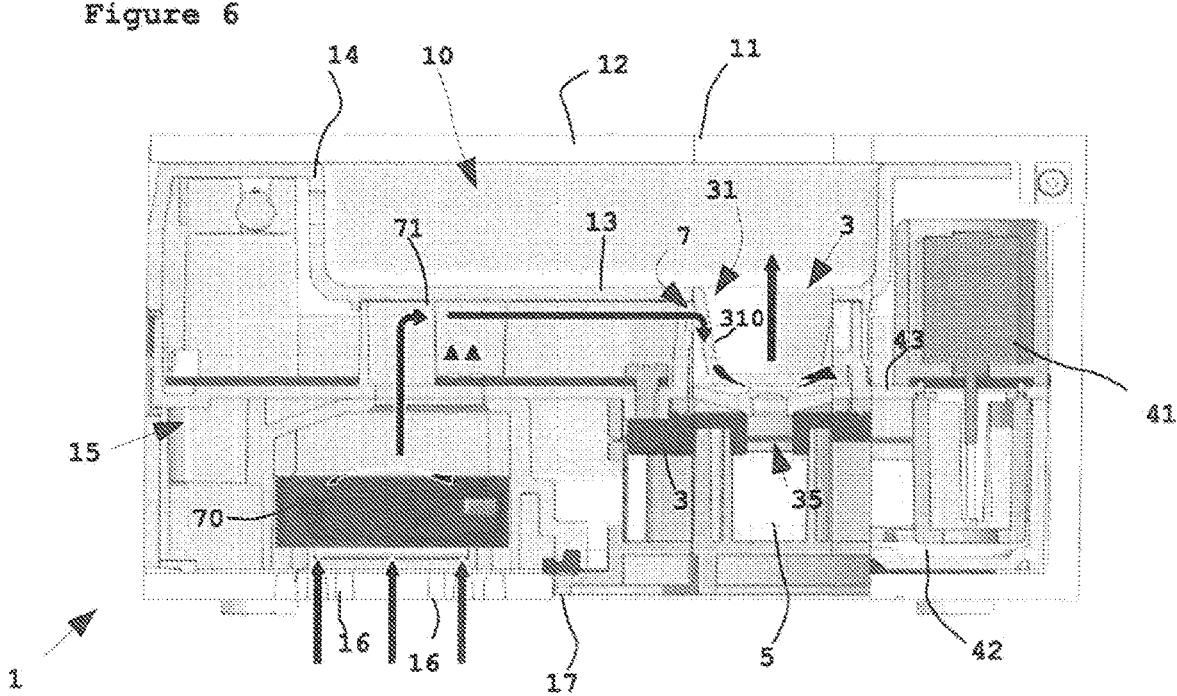
FIG. 6 is a cross-sectional view of the cleaning device of FIG. 4, in which the arrows show the circulation of the air flow during the drying of the earmold.

As shown in FIGS. 4 and 6, the cleaning device 1 includes a reservoir 5 arranged preferably in the inner space 15 of the cleaning device 1 under each cleaning cavity 3. In order to convey the liquid present in the reservoir 5, the cleaning device 1 includes a liquid-flow generator 41. The liquid-flow generator 41 is adapted, on the one hand, to pump the liquid stored in the reservoir 5 via a supply channel 42 and, on the other hand, to project the liquid under constant pressure through an injection channel 43 towards the injection means 4 injecting the liquid into the cleaning cavity 3 continuously at a constant pressure. The injection channel 43 supplies the injection means 4 of the two cleaning cavities 3 the cleaning device 1 includes.

The reservoir 5 also communicates with each cleaning cavity 3 of the cleaning device 1 via the discharge hole 32 connected to a discharge channel 35 communicating with the reservoir 5. Thus, during the cleaning cycle, the flow of liquid discharged through the discharge hole 32 follows the discharge channel 35 in order to join the reservoir 5 (shown in FIG. 4). In order to prevent the earwax removed from the earmold 2 from falling into the reservoir 5, a filter is arranged within the discharge channel 35.

Figure 5:
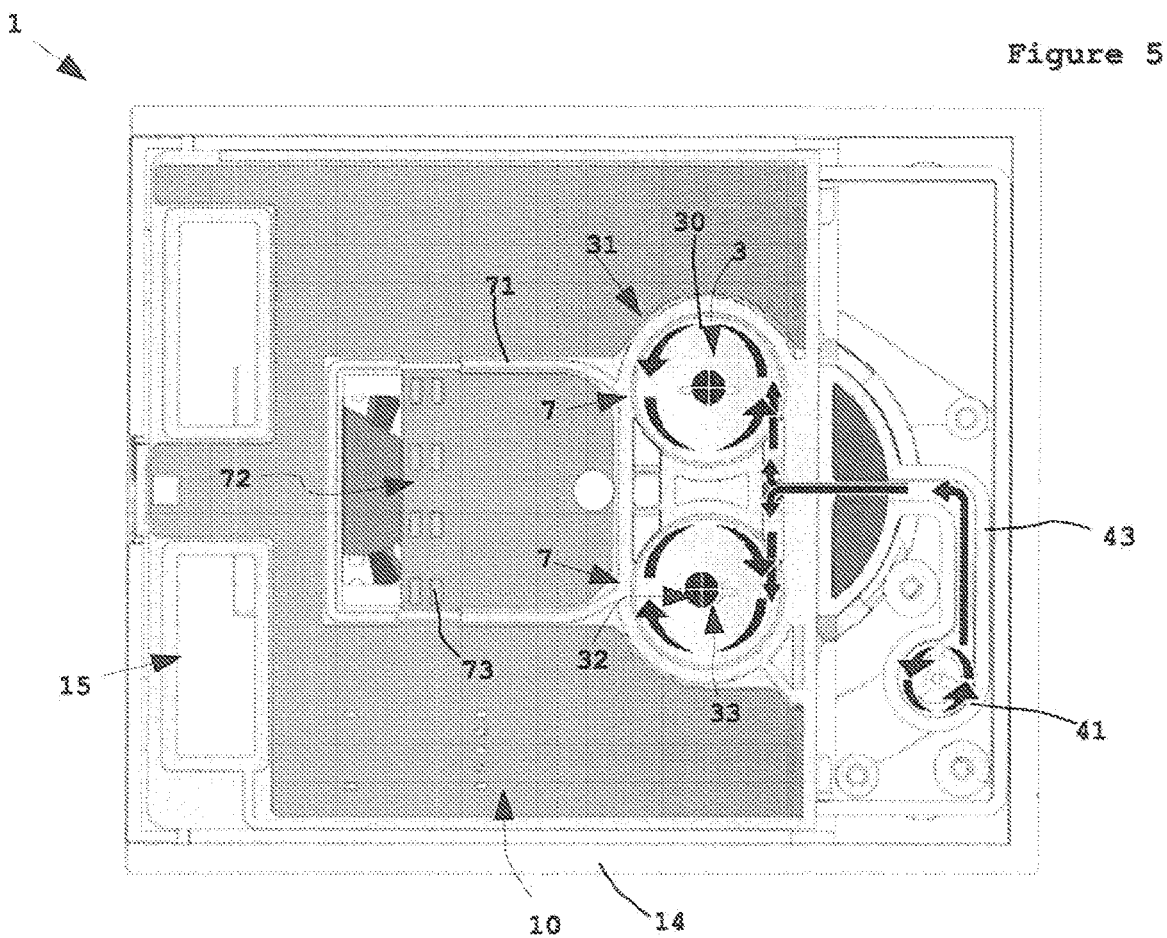
FIG. 5 is a longitudinal cross-sectional view of the cleaning device of FIG. 4, in which the arrows show the circulation of the liquid flow during the cleaning of the earmold.

As shown in FIGS. 4 and 5, during a cleaning cycle, the liquid is used in a closed circuit, i.e. the liquid flow generator 41 generates and continuously injects at a constant pressure a flow of liquid into each cleaning cavity 3. The flow of liquid injected into each cleaning cavity 3 generates a vortex before falling back into the reservoir 5 through the discharge hole 32, while the vortex is maintained by the constant injection of a liquid flow. Once in the reservoir 5, the liquid is again injected into each cleaning cavity 3 by the liquid flow generator 41. The circulation of the liquid flow within the cleaning device 1 during a cleaning cycle is schematically shown in FIGS. 4 and 5 by solid arrows.

It should be noted that the lateral discharge hole 316 communicates with the reservoir 5 through a duct 318 arranged outside the outer skin 311 of the double-skin wall 31.

Advantageously, the cleaning device 1 comprises a plug 6 located between the cleaning cavity 3 and the reservoir 5, and in which the discharge channel 35 is arranged. This plug 6 is movable between three positions, a first, open position, in which the discharge channel 35 is arranged in the axial extension of the discharge hole 32 and the reservoir 5, whereby the liquid can thus circulate from each cleaning cavity 3 to the reservoir 5, a second, closed position, in which the liquid is confined in the reservoir 5, and a third, emptying position, in which the liquid can be drained from the reservoir 5 towards the outside of the cleaning device 1, the emptying is performed by gravity through a siphon 50 obstructed by the plug 6. The plug 6 ensures an easy and practical use of the cleaning device 1. Thus, when the plug 6 is in the closed position, the cleaning device 1 can be transported, the tank 5 can be filled without any risk of leakage of liquid when it is not held horizontally.

Once the cleaning cycle has been completed, in order to quickly dry an earmold 2, the cleaning device 1 includes air-projecting means 7 arranged in the annular space 312 permitting to project swirling air into each cleaning means 3. To this end, the air-projecting means 7 are arranged in the outer skin 311 under the junction 315 between the inner 310 and outer 311 skins of the double wall 31. Thus, the projected air flow enters rotating into the annular space 312. The swirling air flow escapes from the annular space 312 through the cleaning cavity 3 while passing through the transit space 314. This feature permits to eliminate the residual liquid, which remains trapped on the surface of the earmold 2.

In order to generate an air flow supplying the air-projecting means 7, the cleaning device 1 includes in its inner space 15 an air flow generator 70 adapted to suck the ambient air through pores 16 communicating with the outside of the cleaning device 1. Preferably, the pores 16 are arranged in the lower face 17 of the cleaning device 1. The air flow generator 70 then projects an air flow through a vent duct 71 conveying the air flow to the air-projecting means 7. Preferably, the vent duct 71 has an L-shaped cross-section so as to guide the air flow as directly as possible to the air-projecting means 7, thus preserving the intensity of the air flow and the drying efficiency for the earmold 2. The conveying of the air flow during the drying of an earmold 2, from the air-flow generator 70 to the cleaning cavity 3 is schematically shown by solid arrows in FIGS. 6 and 7.

Figure 7:
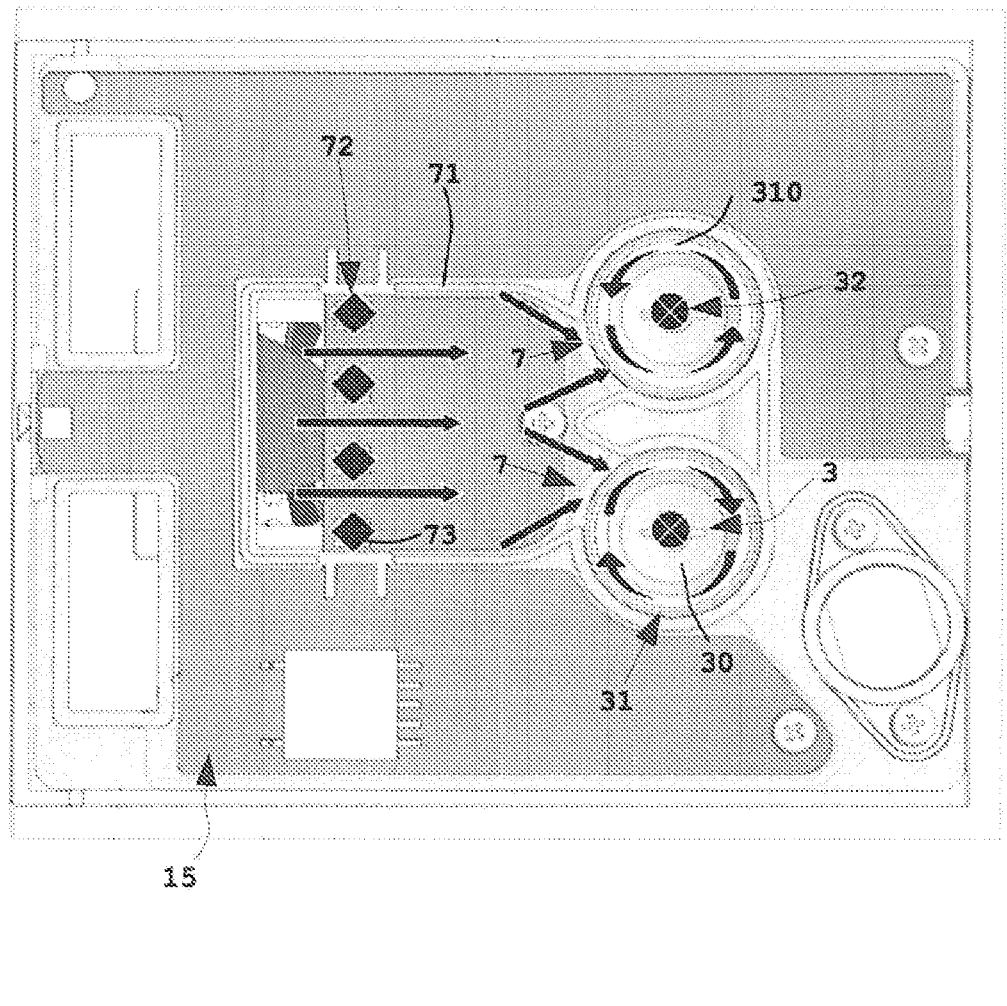
FIG. 7 is a longitudinal cross-sectional view of the device of FIG. 4, in which the arrows show the circulation of the air flow during a drying of the earmold.
Figure 10:
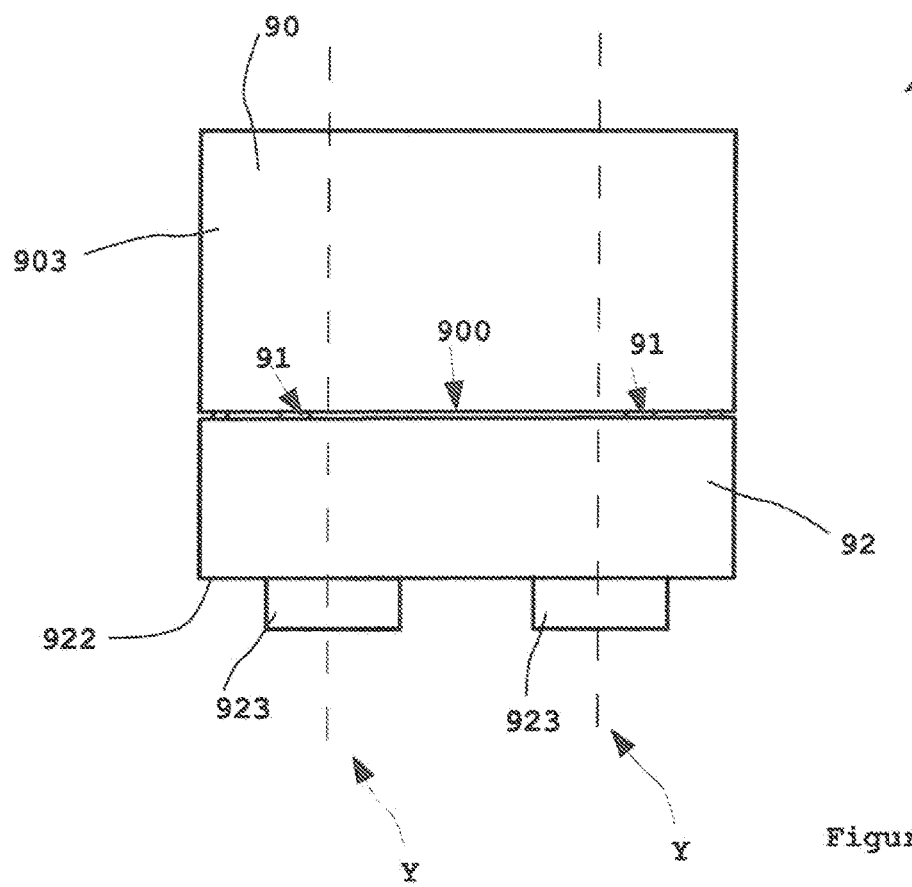
FIG. 10 is a front elevation view of the refilling unit of FIG. 8, the cap being in the percussion position.
Figure 11:
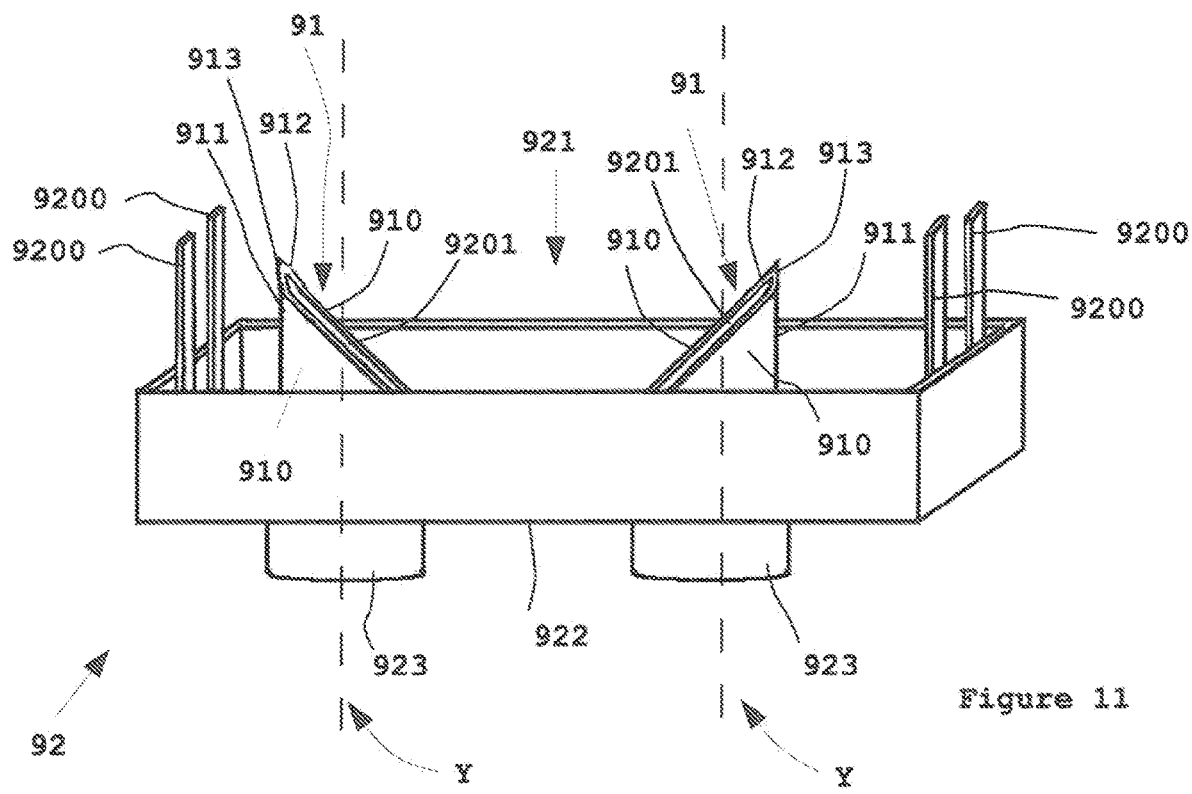
FIG. 11 is a perspective front view of the cap of the refilling unit of FIG. 8.
Figure 12:
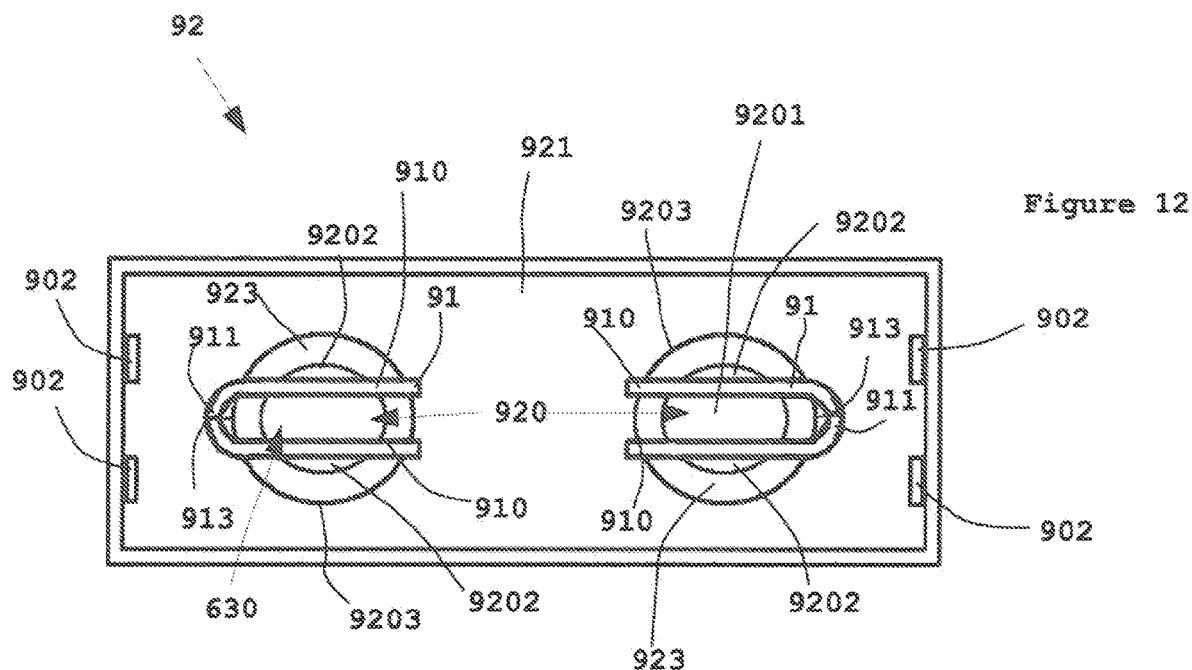
FIG. 12 is a top plan view of the cap of the refilling unit of FIG. 8.

Advantageously, according to an additional feature of the invention shown in FIGS. 6 and 7, the cleaning device 1 comprises means for heating 72 the air flow. Preferably, these heating means are located in the vent duct 71 upstream of the air-projecting means 7. Heating the air flow permits to eliminate more quickly, by evaporation, the residual liquid, which is located on the surface of the earmold 2 after a cleaning cycle. In this example, the means for heating 72 the air flow are formed by electrical resistors 73, however, the means for heating 72 the air flow can be formed by any electrical, electronic, mechanical, thermal means capable of heating an air flow. The heating of the air flow is schematically shown by solid triangles in FIG. 6 and solid diamonds in FIG. 7.

It should be noted that in a specific configuration of the cleaning device 1, the air-projecting means 7 can operate during the cleaning cycle and at the same time as the liquid-injecting means 4. Indeed, when properly parameterized, the air flow generator 70 is quite capable of generating an air flow adapted to participate in the control of the vortex of liquid cleaning the earmold 2.

According to an additional feature of the invention shown in FIGS. 4 and 6, in addition to the disinfecting properties of the cleaning liquid, the cleaning space 10 is provided with a UVC lamp 8 adapted to diffuse the UVC waves within the cleaning space 10 and the cleaning cavity 3. Thus, a hearing aid 20 arranged in the cleaning space 10 when the cover 12 is closed will be disinfected by UVC irradiation. This feature permits to end each cleaning cycle, once the earmold 2 is dry, with a disinfection of all the elements of the hearing aid 20 (earmold 2 and eventually the ear contour 23 when the prosthesis includes one). The UVC irradiation of the hearing aid 20 has the advantage of eliminating irritating or allergenic elements, which are always present after the cleaning cycle and to thus reduce the irritations of the auditory canal and the ear contour of the user of the hearing aid 20.

The use of a heated air stream to eliminate by evaporation the residual liquid present on the surface of the earmold 2 results into a loss of the quantity of liquid present in the reservoir 5. In order to prevent the user from initiating a cleaning cycle while the quantity of liquid present in the reservoir 5 is insufficient, the reservoir 5 is provided with means for detecting the level of liquid. These detecting means can be formed by resistive sensors or any other mechanical or electronic means capable of triggering when the level of liquid falls below a predefined threshold level. The cleaning device 1 also includes warning means (for example a sound signal, a visual signal on a screen, etc.) adapted to signal to the user that he must drain and refill the reservoir 5.

In addition, the cleaning liquid must be changed after a number of cleaning cycles, or when the level of liquid present in the reservoir becomes insufficient, for example as a result of losses of liquid by evaporation.

In order to fill the reservoir 5 arranged in the inner space 15 of the cleaning device 1, the applicant has developed a refilling unit 9 having a simple and inexpensive structure.

This refilling unit 9 advantageously permits to proceed to an easy, clean filling without splashing of the tank 5 of the cleaning device 1.

To this end, at least one cleaning cavity 3 is used as an interface for causing the cleaning liquid to transit between the refilling unit 9 and the reservoir 5.

Figure 13:
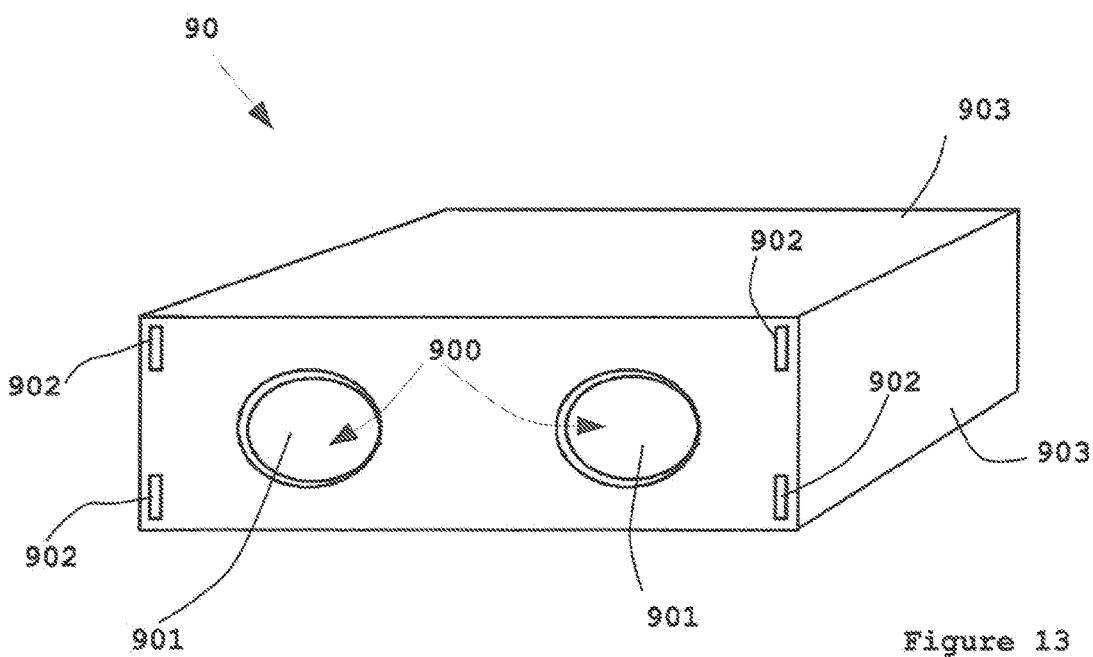
FIG. 13 is a bottom plan view of the tank of a refilling unit of FIG. 8.

In the example shown in FIGS. 8 to 10 and 13, the refilling unit 9 includes a tank 90 in the form of a pad. Of course, other shapes can also be considered, such as cubic, spherical, cylindrical, etc. shapes. With reference to FIG. 13, the tank 90 includes on one of its faces two openings 900 arranged in such a way that they can each be located along the axis X of the cleaning cavity 3 of the cleaning device 1 when the refilling unit 9 is located in front of the cleaning space 10.

In order to keep the cleaning fluid tightly inside the tank 90, the openings 900 are each closed by an impervious lid 901, which holds the liquid inside the tank 90 as long as it is neither peeled nor perforated.

In the present example, the lid 901 is capable of being perforated by a perforator 91 in order to release the liquid from the tank 90 and to permit it to flow through the openings 900. It should be noted that the tank 90 could also contain a tight pocket filled with cleaning liquid and a portion of which would therefore be likely to serve as a lid closing the openings 900. Likewise, such a pocket would therefore be likely to be perforated by a perforator 91 in order to release the liquid and to permit its flowing through the openings 900.

As shown in FIGS. 8 to 12, the refilling unit 9 is in addition provided with a cap 92 covering the openings 900, provided with two channels 920 each extending along the axis Y of an opening 900. The cap 92 constitutes in fact a connecting interface between the refilling unit 9 and the cleaning device 1 to be refilled. It includes an inner face 921 arranged in front of the openings 900 of the tank 90 and an outer face 922 intended to be placed into contact with the cleaning device 1, during the refilling of the latter.

In order to release the liquid contained in the tank 90 of the refilling unit 9, the cap 92 includes two perforators 91 adapted to each perforate a cap 901 and to let the liquid flow once the cap 901 has been perforated.

In fact, each perforator 91 extends from the inner face 921 of the cap 92 towards the openings 900 of the tank 90. In addition, the cap 92 is movable relative to the tank 90 between a preliminary position (shown in FIGS. 8 and 9), in which the perforators 91 are spaced apart from each opening 900, and a percussion position (shown in FIG. 10), in which each perforator 91 extends into an opening 900 through the so perforated lid 901. The preliminary position corresponds to the position in which the cap 92 is located before using the refilling unit 9, while the percussion position is reached when the refilling unit 9 is used.

In this example, the cap 92 includes two pairs of rails 9200 each extending parallel to the axis Y of an opening 900. These rails 9200 are designed to cooperate with sliding grooves 902 adequately arranged on the wall 903 of the tank 90. These features permit the cap 92 to be movable in translation with respect to the tank 90 in a direction parallel to the axis Y of an opening 900.

Each rail 9200 cooperates with a sliding groove 902 so that the cap 92 moves between its two positions. Thus, the cap 92 can both act as a protector for a lid 900 when it is in the preliminary position and the refilling unit 9 must be kept intact while waiting for its use, and as a perforator for a lid 900 when it is in the percussion position, as will be described below.

Furthermore, the perforators 91 of the cap 92 are advantageously shaped so as to each define a cannula for discharging the cleaning liquid contained in the tank 90 through each opening 900 of the tank 90 and each channel 920 of the cap 92. To this end, each perforator 91 has two lateral faces 910 connected to each other by a base 911 and extends in the direction of movement of the cap 92 in a plane perpendicular to the inner face 921 of the cap 92. The free edge 912 of the base 911 of each perforator 91 is in addition shaped so as to define a perforating tip 913 projecting at the level of the base 911 and capable of perforating a lid 900. Furthermore, thanks to its structure and its position transverse to a channel 920, each perforator 92 compartmentalizes the latter into three zones, a central liquid channeling zone 9201 located between its two lateral faces 9202 and two lateral zones 9202 located between each lateral face 910 and the edge 9203 of the channel 920. It should be noted that a perforator 91 may have different shapes insofar as it extends from the internal face 921 of the cap 92 towards the openings 900.

Thus, when the cap 92 passes from its preliminary position to its percussion position, the perforating tip 913 of the perforator 91 enters into contact with a lid 900, perforates it, winds it up and releases the liquid contained in the tank 90. Advantageously, each lateral zone 9202 performs an air intake permitting the liquid to flow through the central zone 9201.

In order to prevent any undesired movements of the cap 92 from its preliminary position to its percussion position, blocking means are arranged at the junction between the cap 92 and the tank 90. These blocking means are designed removable and permit the cap 92 to remain in the preliminary position until the refilling unit 9 is being used. The blocking means can for example be defined by a plastic strap arranged at the junction between a lid 900 and the tank 90, this strap blocking the movement of the cap 92.

In the example shown in FIGS. 8 to 12, the cap 92 furthermore includes two sleeves 923 extending on its outer face 922 and defining the channel 920. Each sleeve 923 is shaped in a way complementary to the cleaning cavity 3 of the cleaning device 1. Thus, the sleeves 923 constitute connecting means between the refilling unit 9 and the cleaning device 1.

When the warning means of the cleaning device 1 indicate to the user that it is necessary to empty and re-fill the cleaning liquid reservoir 5, the user causes the plug 6 to pass into its emptying position in order to perform the discharge of the reservoir 5. After the emptying, the user brings the plug 6 into its open position, in which the discharge channel 35 and the discharge opening 32 are located in the axial extension of the reservoir 5, it is then possible to fill the latter with the aid of the refilling unit 9 by gravity using the cleaning cavities 3 of the cleaning device 1 as an interface with the reservoir 5.

In order to proceed to the refilling of the reservoir 5 of the cleaning device 1, the means for blocking the movement of the cap 92 should be removed before each sleeve 923 of the cap 92 is positioned within a cleaning cavity 3 so that the refilling unit 9 encases with the cleaning device 1. Thus, each opening 900 of the tank 90 is aligned with a channel 920 of the cap 92, a liquid discharging hole 32, which is in turn axially aligned with a discharge channel 35, providing access to the reservoir 5.

Finally, the user applies a vertical pressure to the tank 90 of the refilling unit 9. Under the action of this pressure, the cap 92 moves from its preliminary position to its percussion position. Each perforator 91 is then capable of entering into contact with a lid 901, pierces it and controls, due to its arrangement and its shape, the flow of the cleaning liquid contained in the tank 90 of the refilling unit 9 towards the reservoir 5 of the cleaning device 1. Thus, the flow of the cleaning liquid occurs by gravitation.

In the present example, the cleaning cavity of the cleaning device 1 fulfills two functions, a function of cleaning a hearing aid (20) and its earmold (2) and a function of filling the reservoir 5.

Thanks to the invention and the complementarity between the refilling unit 9 and the cleaning device 1, it is thus possible to carry out a clean filling of the reservoir 5 without splashing and without loss of liquid.

The invention claimed is:

1. A device for cleaning a hearing aid by touching with a liquid, said device comprising:
   an inner skin wall having an inner skin upper end and an inner skin lower end with an inner skin base opening, said inner skin lower end being opposite said inner skin upper end so as to form a cleaning cavity receiving an earmold; and
   an outer skin wall having an outer skin upper end and an outer skin bottom with an outer skin bottom opening, said outer skin bottom being opposite said outer skin upper end so as to form a bottom of said cleaning cavity,
   wherein said inner skin upper end is joined to said outer skin upper wall at a junction,
   wherein said inner skin lower end has a diameter smaller than said outer skin lower end, wherein said outer skin wall surrounds said inner skin wall so as to form an annular space between said inner skin wall and said outer skin wall, wherein said inner skin base opening and said outer skin bottom of said outer skin wall form a transit space therebetween, said annular space being in fluid connection with said cleaning cavity through said transit space, and wherein said outer skin wall is comprised of a means for injecting liquid, said means for injecting being in fluid connection with said annular space.

2. The cleaning device, according to claim 1, wherein said outer skin wall is further comprised of a lateral discharge hole at a level higher than said means for injecting so as to permit discharging an excess of liquid circulating between said inner skin wall and said outer skin wall.

3. The cleaning device, according to claim 1, wherein means for injecting are tangent to said outer skin wall so as to project liquid tangentially along said outer skin wall in said annular space.

4. The cleaning device, according to claim 1, further comprising:
a reservoir being provided with a plug and being in fluid sealed connection with said cleaning cavity in a closed position, in which liquid is confined in said reservoir, and being in fluid connection with said cleaning cavity in an open position, in which liquid circulates between said cleaning cavity and the reservoir, said reservoir having an emptying position, in which liquid is drained from said reservoir.

5. The cleaning device, according to claim 4, wherein the reservoir comprises means for detecting a level of liquid so as to trigger emission of a warning signal when the level of liquid present inside said reservoir reaches a predefined threshold level.

6. The cleaning device, according to claim 1, wherein the bottom comprises protruding receiving means for the earmold.

7. The cleaning device, according to claim 1, wherein said junction defines a closed top of said annular space.

8. The cleaning device, according to claim 1, wherein the outer skin wall is further comprised of means for projecting air into said annular space.

9. The cleaning device, according to claim 8, further comprising: a heating means for projected air flow of said means for projecting air into said annular space.

10. The cleaning device, according to claim 1, further comprising: a UVC lamp so as to diffuse UVC waves towards the hearing aid and so as to perform a disinfection by UVC irradiation.

11. A device, comprising:
a cleaning device, according to claim 1, further comprising:
a reservoir being provided with a plug and being in fluid sealed connection with said cleaning cavity in a closed position, in which liquid is confined in said reservoir, and being in fluid connection with said cleaning cavity in an open position, in which liquid circulates between said cleaning cavity and the reservoir, said reservoir having an emptying position, in which liquid is drained from said reservoir,
wherein the reservoir comprises means for detecting a level of liquid so as to trigger emission of a warning signal when the level of liquid present inside said reservoir reaches a predefined threshold level; and
a cleaning-liquid refilling unit being comprised of a sleeve removeably engaged with said reservoir through said cleaning cavity so as to transfer cleaning fluid from said refilling unit to said reservoir.

12. The device, according to claim 11, wherein the refilling unit is further comprised of:
a tank provided with an opening;
a lid covering said opening; and
connection means to perforate said lid when connected to said cleaning cavity.

13. The device, according to claim 11, wherein the refilling unit is further comprised of:
a cap having a channel,
a perforator facing said lid and said connection means so as to make said cap movable relative to said tank between a preliminary position, in which the perforator is moved away from the opening, and a percussion position, in which the perforator perforates the lid and releases the liquid through the channel.

14. The device, according to claim 13, wherein said perforator is comprised of a cannula so as to discharge cleaning liquid contained in said tank through said channel.

15. The device, according to claim 13, wherein perforator is comprised of two lateral faces connected to each other by a base having a perforating tip so as to extend in a direction of displacement of said cap and so as to perforate said lid.

16. A device for cleaning a hearing aid by touching with a liquid, said device comprising:
an inner skin wall having an inner skin upper end and an inner skin lower end with an inner skin base opening, said inner skin lower end being opposite said inner skin upper end so as to form a cleaning cavity receiving an earmold;
an outer skin wall having an outer skin upper end and an outer skin bottom with an outer skin bottom opening, said outer skin bottom being opposite said outer skin upper end so as to form a bottom of said cleaning cavity,
wherein said inner skin lower end has a diameter smaller than said outer skin lower end,
wherein said outer skin wall surrounds said inner skin wall so as to form an annular space between said inner skin wall and said outer skin wall, and
wherein said outer skin wall is comprised of a means for injecting liquid, said means for injecting being in fluid connection with said annular space; and
a reservoir being provided with a plug and being in fluid sealed connection with said cleaning cavity in a closed position, in which liquid is confined in said reservoir, and being in fluid connection with said cleaning cavity in an open position, in which liquid circulates between said cleaning cavity and the reservoir, said reservoir having an emptying position, in which liquid is drained from said reservoir.

17. An assembly, comprising:
a cleaning device,
wherein said cleaning device comprises:
an inner skin wall having an inner skin upper end and an inner skin lower end with an inner skin base opening, said inner skin lower end being opposite said inner skin upper end so as to form a cleaning cavity receiving an earmold;
an outer skin wall having an outer skin upper end and an outer skin bottom with an outer skin bottom opening, said outer skin bottom being opposite said outer skin upper end so as to form a bottom of said cleaning cavity,
wherein said inner skin lower end has a diameter smaller than said outer skin lower end, wherein said outer skin wall surrounds said inner skin wall so as to form an annular space between said inner skin wall and said outer skin wall, and wherein said outer skin wall is comprised of a means for injecting liquid, said means for injecting being in fluid connection with said annular space; and a reservoir being provided with a plug and being in fluid sealed connection with said cleaning cavity in a closed position, in which liquid is confined in said reservoir, and being in fluid connection with said cleaning cavity in an open position, in which liquid circulates between said cleaning cavity and the reservoir, said reservoir having an emptying position, in which liquid is drained from said reservoir; and a cleaning-liquid refilling unit being comprised of a sleeve removeably engaged with said reservoir through said cleaning cavity so as to transfer cleaning fluid from said refilling unit to said reservoir.

* * * * *